United States Patent [19]

Robinson

[11] Patent Number: 4,473,559

[45] Date of Patent: Sep. 25, 1984

[54] METHOD AND COMPOSITION FOR RETARDING RED BLOOD CELL SICKLING

[76] Inventor: Larry H. Robinson, 1904 Alabama, Baytown, Tex. 77520

[21] Appl. No.: 476,569

[22] Filed: Mar. 18, 1983

Related U.S. Application Data

[63] Continuation-in-part of Ser. No. 291,799, Aug. 13, 1981, abandoned, which is a continuation-in-part of Ser. No. 183,820, Sep. 3, 1980, abandoned.

[51] Int. Cl.$^3$ ............................................. A61K 35/78
[52] U.S. Cl. ................................................... 424/195
[58] Field of Search ..................... 424/195; 260/245.91

[56] References Cited

U.S. PATENT DOCUMENTS 3,102,891  9/1963  Allen .............................. 260/245.91

*Primary Examiner*—Stanley J. Friedman
*Assistant Examiner*—John Rollins
*Attorney, Agent, or Firm*—Arnold, White & Durkee

[57] ABSTRACT

A mixture of compositions for reducing red blood cell sickling is disclosed. This process utilizes porphyrinic and chlorophyllic compounds derived from dehydrated legumes and cereal grasses. After processing, the product of interest is a free flowing crystalline solid and has a purple color when dissolved in methanol. It is yellow when dissolved in water, has a strong absorption band near 400 millimicrons when dissolved in either water or methanol and has lesser absorption bands at other wavelengths, is free of esters or ketones and is believed to be an alkali metal salt, the preferred salt being potassium carboxylic acid salt, and wherein the active agent is substantially free of magnesium and includes a trace amount of paramagnetic impurities.

2 Claims, No Drawings

METHOD AND COMPOSITION FOR RETARDING RED BLOOD CELL SICKLING

BACKGROUND OF THE INVENTION

This is a continuation-in-part application of Ser. No. 291,799, filed Aug. 13, 1981, now abandoned, which itself is a continuation-in-part application of Ser. No. 183,820, filed Sept. 3, 1980, now abandoned.

The present invention relates to screening potential medical and therapeutic agents; and more particularly it relates to methods to determine whether a person having the disease sickle cell anemia is potentially amenable to treatment with therapeutic agent.

Sickle cell anemia is a recessive hereditary disorder, essentially confined to Negroes, although persons descended from Mediterrean ancestorage may also exhibit the trait. From 7 to 10 percent of American Negroes have blood containing a defective hemoglobin termed HbS; among West African Negroes this percentage may be as high as 40 percent. A person affected with sickle cell disease will have predominantly the HbS variant of hemoglobin, while persons with the sickle cell trait have a genetic mixture of both HbS and normal hemoglobin.

When the abnormal hemoglobin HbS is exposed to low concentration of oxygen, the hemoglobin molecule precipitates into long crystals inside the red blood cells. These crystals elongate the cell giving the cell the appearance of a sickle as opposed to the cell's normal biconcave disc or doughnut shape. Hence the term "sickling" is applied to such a cell conformation activity. In the deoxygenated form the HbS is less soluble than normal hemoglobin, consequently the viscosity of the whole blood cell increases, resulting in cell aggregation and obstruction of subsequent blood flow through the capillaries. The precipitated hemoglobin also damages the cell membranes, which become exquisitely fragile, leading to serious anemia or rupture.

Sickle cell patients frequently get into a vicious cycle or crisis, whereby low oxygen concentration in the tissues, often induced by stress or fatigue, causes sickling. This in turn results in impeded blood flow through the tissue, causing further decrease in oxygenation to the tissue. Circulatory complications include leg ulcers, bone infection, tissue necrosis, cardiac enlargement, hematuria, and associated secondary infections.

Heretofore, treatment for sickle cell crisis was symptomatic consisting mainly of bed rest, analgesic administration, and blood transfusions for severe hemolytic crisis. There is no known cure for this genetic disease, nor has there been, heretofore, any safe, effective and reliable anti-sickling agent available for in vivo administration. Accordingly, there is a need for a treatment to retard in the first instance the sickling of red blood cells, as a primary treatment for sickle cell crisis and prophylaxis. Moreover, before in vivo treatment is initiated, there is a need to know whether a particular patient is amenable to treatment with a selected anti-sickling agent. This invention presents an in vitro method of assessing whether a patient having sickle cell anemia disease is potentially amenable to treatment with the selected anti-sickling agent.

SUMMARY OF THE INVENTION

This disclosure is directed to a mixture of compounds suitable for retarding or reducing red blood cell sickling. As found in the patent of Allen, U.S. Pat. No. 3,102,891, a process of preparing new compositions of porphyrinic and chlorophyllic compounds is disclosed. It is believed that the processes disclosed therein and the products obtained thereby have significant medicinal and therapeutic value.

With limitations of Allen in view, this disclosure reveals a method of utilizing a mixture of compounds obtained by the process of Allen which is uniquely able to retard red blood cell sickling and which mixture of compounds is characterized by the following attributes: the product thereof is a mixture of compounds derived from porphyrinic or chlorophyllic compositions; the mixture contains from 35 to 65 percent porphyrinic compounds and the balance is substantially chlorophyllic compounds; is purple in color when dissolved in methanol, yellow color when dissolved in water; has a strong absorption band near 400 millimicrons when dissolved in methanol or water and has other but lesser absorption bands at other wavelengths; and is believed to be an alkali metal salt, the preferred salt being potassium carboxylic acid salt of porphyrinic compounds; the mixture further being free of esters and ketones; and having the form of a free flowing solid, being soluble in polar solvents and insoluble in non-polar solvents. The chlorophyllic molecule functions somewhat as a chelating agent which is able to bind paramagnetic impurities. The final mixture of compounds includes mintute portions of magnesium.

The present invention provides an in vitro method for retarding the sickling of red blood cells, which involves contacting the products derived from the Allen process with a blood sample taken from a host susceptible to red blood cell sickling. The methods of the present invention are useful in determining whether the host is potentially amenable to in vivo treatment with the anti-sickling composition.

DETAILED DESCRIPTION OF THE PREFERRED EMBODIMENTS

A. Method of Manufacture

The present procedure utilizes cattle forage crops. Typically, this includes various and sundry grasses used in feeding cattle. A list range of legumes and cereal grasses includes oats, wheat, alfalfa, barley, rye and other range grains. As mentioned in the Allen disclosure, U.S. Pat. No. 3,102,891 (incorporated herein by reference), the list of grasses is reasonably broad. To attain the desired compositions the legumes and grasses are ideally cut before flowering which upon subsequent dehydration have optimum protein and vitamin A content and have a characteristic green color indicative of the presence of chlorophyll.

Beginning with a sample of crushed and dehydrated alfalfa (obtained from a local feedstore in Houston, Texas comprising alfalfa species *Medicago sativa* grown and harvested from the Southeast Texas region) weighing 1.0 kilogram, 1.0 liter isopropanol and about 4.0 liters of n-heptane were all placed in a porcelain vessel and agitated for ninety minutes using a mechanical stirring device. The n-heptane is selected from the group of chain hydrocarbons of up to about twelve carbon atoms, and the isopropanol is a mono-hydric alkyl alcohol which contains ten or fewer carbon atoms. It will be observed that the liquids are mixed in a ratio of four to one, alkane to alcohol; this falling within the range of about two to one up to about eight to one suggested by Allen. This falls within the definition of the first step of the Allen process. Interestingly, the several initial steps in the method of manufacture and extraction are similar to the Allen process up to the last few steps where additional steps not disclosed in Allen are implemented to aid in the chemical characterization of the product. To this end, the beginning steps of Allen are incorporated by reference.

The mixture of alfalfa and solvents is then filtered through a suitable filter, the ideal filter being a Whatman No. 1 paper and the filtrate is collected in a suitably sized resin kettle. The next step is to distill the filtrate to a final volume of about 200 milliliters at about 98° C. This typically represents a reduction from about 3,000 milliliters to about 200 milliliters. This drives off the mixed solvents. The 200 milliliter batch which remains after partial distillation is then mixed with about 800 milliliters of methanol in the resin kettle and is redistilled again to a somewhat reduced volume at a reduced temperature. The final volume should be about 500 milliliters which distillation is obtained at about 65° C.

While this mixture remains hot, a solution of potassium hydroxide (KOH) is added. A typical solution is about ten percent KOH dissolved in methanol. This basic material raises the pH substantially and the pH is adjusted upward to about 11.7. According to Allen, the alcoholic pH can be in the range of about 11.5 to about 11.8. Allen further supposes that the long chain hydrocarbon has been removed in a solvent exchange. Accepting this premise, the initial solvents of isopropanol and n-heptane have been exchanged for methanol.

Once the pH of about 11.7 has been obtained without going above that value, the solution is allowed to cool for about four hours. Thereafter, it is filtered again and the ideal filter is a Whatman No. 1 paper.

The next step is to perform an extraction from the filtrate obtained from the previous filtration step. It is supposed at this point that the initial alfalfa compounds have now been saponified and are in solution in the alkanol. An extraction by liquid-liquid extraction removes the lipids or oil soluble materials, and is preferably accomplished by pouring the filtrate through a column containing about 1,000 milliliters of n-heptane. The column used in one procedure measured 24 inches (60 cm) in height by 4 inches (10 cm) in diameter. The extraction is accomplished with gentle swirling whereupon the phases are permitted to separate.

The product obtained from the liquid-liquid extractions includes a methanol layer. The methanol layer is separated after the extraction step. It is then distilled at a temperature of about 100° C. whereupon 500 milliliters of deionized water are added. The water is stirred and a suitable mineral or inorganic acid is added to lower the pH to about 3.5. One acid is HCl. This solution is then permitted to stand for up to about three hours. After standing, this aqueous mixture is next filtered through a filter cake formed of diatomaceous earth. One brand or grade is sold under the trademark Celite. The filtrate is discarded and the filtered materials are washed with liberal quantities of deionized waters. After washing, and subsequent refiltration, the recovered solids are air dried at room temperature.

The filter cake which is obtained from the previous filtration step includes solids which solids contain the alfalfa extract of interest. These solids are dispersed in about 500 milliliters of methanol, and the pH is then raised to about 8.5. The pH is raised by again adding KOH in methanol until a pH of 8.5 is achieved. This mixture is then filtered again through a Whatman No. 1 paper, and the filtrate is captured in a large resin kettle. The filtrate is distilled to remove the methanol completely. This should be accomplished at a temperature in the range of about 90° C., but it should not exceed 100° C. The remnant after distillation is then dried in a vacuum oven at about 70° C. under a pressure of 50 torr absolute.

At this juncture, it should be noted that the dry product extract is a colored product in the range of blue to black and is a viscous to waxy substance. It is soluble in water and lower alcohols. It is insoluble in ketones and alkanes. The mixture when dissolved in water as a 1 percent by weight solution at 20° C. exhibits a pH of 8.5. This product (hereinafter labelled the "Allen product") is useful for in vitro experimentation to determine whether a patient with sickle cell anemia is potentially amenable to in vivo treatment with ten anti-sickling agent.

B. Product Isolation and Testing

In order to facilitate characterization of the products obtained from the processes of Allen, further purification operations were applied to the recovered product. A high pressure liquid chromatography separation was next accomplished using a Whatman Magnum ODS bonded phase column. The solvent that was used was 75% methanol and 25% water. The alfalfa extract was separated into nine fractions and the remnant represented the tenth fraction which was removed from the column with 100% methanol. The sixth and eighth fractions obtained after separation both had a characteristic purple color when dissolved in methanol. They both showed significant activity as an anti-sickling agent. The methanol in fractions six to eight was removed under the vacuum. Water, to the extent that it was present, was also removed by freeze drying.

Testing of the sixth and eighth fractions for chemical characteristics yielded the following information. It is believed these fractions include porphyrins which are four pyrrole rings linked at alpha positions by methyne groups. The porphyrins isolated in fractions six and eight are purple when dissolved in methanol and yellow when dissolved in water. The eighth fraction which showed the strongest anti-sickling activity has a strong absorption band in the visible range near 408 millimicrons and weaker absorption bands at 637, 590, 565 and 501 millimicrons when dissolved in methanol. Absorption measurements were made with a Perkin-Elmer Hitachi Model 200 UV-visible spectrophotometer. The eighth fraction has the same absorption spectra in neutral water, basic water or acidic water. The strongest absorption band of the eighth fraction in water is located at 400 millimicrons. The absorption spectra of the sixth fraction is similar except the strongest absorption band is located 400 millimicrons when dissolved in methanol or water. It is believed that there is little significance to the difference in the location of the strongest absorption bands when measured at 400 and 408 millimicrons. As described herein and is claimed below, reference to the strongest absorption band near 400 millimicrons is intended to include the actual measurement of 408 millimicrons. After freeze drying, fractions six and eight were dark red to brown in color.

Further testing showed that the sixth and eighth fractions do not contain esters, and they do not contain ketone groups. Both fractions are thought to include potassium salts of a carboxylic acid salt, and both fractions were extremely low in magnesium measuring less than 0.04% by a weight. It will be recalled that porphyrin type compounds function as chelating agents. While chlorophyll includes a chelated magnesium ion, the product obtained and tested in fractions six and eight appears to be extremely low in magnesium. Accordingly, this implies that the chlorophyllic content is markedly reduced in contrast with the other porphyrinic content. Testing with nuclear magnetic reasonance techniques could not be run because of the presence of trace paramagnetic impurities which interfere with the NMR spectroscopy.

It is further reasoned from the tests that the chlorophyll molecule has been modified by the removal of all organic esters.

It appears that two important factors relate to the successful preparation of the sixth and eighth fractions. At the intermediate step where the pH is raised typically to 11.7, an alternate batch was prepared where the pH was raised to 12.5. The excessive pH appears to have completely suppressed the formation of the anti-sickling agent. By contrast, considering the same step, a third batch was prepared where the pH was raised to 11.7. However, the mixture was refluxed for three hours prior to cooling. Again, the anti-sickling agent was substantially not found. Only a slight activity was obtained. From these two batches, it is reasoned that the overextended exposure to a high pH, (thought to be above 11.8) for an extended interval, or both prevent the formation of the anti-sickling agent.

The Allen product, and fractions six and eight, as recovered above, utilizing the procedure described in this specification, are each believed suitable for treatment sickle cell anemia as, for instance, by oral ingestion or by an intraveneous injection with a pharmaceutically suitable solvent of no significance to the blood system such as dextrose, normal saline, etc. The therapeutic concentration chosen should be sufficient to inhibit sickling of red blood cells to the extent of at least about 30%. The preferred composition for administration is the Allen product extract rather than the fractionated mixtures, since fractionation process is extremely time consuming and expensive to perform without yielding a significant increase in activity.

Application has found from laboratory experimentation that the Allen product extract disclosed above yields impressive data indicating anti-sickling activity and that such patients may be amenable to subsequent in vivo treatment with the anti-sickling agent provided by the Allen product.

Some of those experiments are reported in the examples which follow.

EXAMPLE I

The recovered extract material obtained from the method of manufacture described above in Section A was tested using a standard bioassay test relating to the kinetics of sickling which is described by J. P. Harrington and R. L. Nagel in the *Journal of Laboratory and Clinical Medicine*, St. Louis, Volume 90, Number 5, Pages 863–872. In this test, 10 milliliters human whole blood of type HbAS red blood cells were incubated thirty minutes in a total of 25 milliliters of phosphate buffered saline solution (pH 7.4) containing 0.86 mg/ml of the tested extract. Next the red blood cells were deoxygenated with sodium dithionite at ice temperature. The extent of sickling in samples was visually observed and determined through a Zeiss microscope. Observations were taken at timed intervals. Anti-sickling activity was evaluated by assessing the extent of red blood sickling at $t_{\frac{1}{2}}$ comparing the percent retardation of sickling in the test sample with the extent of sickling apparent in control samples (control samples of HbAS were subjected to deoxygenation but had no test extract added). The $t_{\frac{1}{2}}(50\%)$ is the time for one-half of the HbS red blood cells in a sample comprising HbAS type red blood cells to sickle. An anti-sickling agent will have the effect of increasing both the number of normal biconcave shaped cells and the $t_{\frac{1}{2}}(50\%)$, relative to the control.

Results:

|  | % Sickled Cells After 80 Minutes | $t_{\frac{1}{2}}$ seconds |
|---|---|---|
| Control Sample | 80 | 30 |
| Extract Treated Sample | 52 | 720 |

EXAMPLE II

Effect on Gelation: Minimum gelling concentration is the minimum concentration of total hemoglobin at which a mixture containing sickle cell HbS hemoglobin forms a gel upon complete deoxygenation. Polymerization produces intracellular gel on deoxygenation. Solubility of deoxygenated hemoglobin solution was determined as gelling occurs by the sedimentation method devised by Hofrichter et al, *Proc. Natl. Acad. Sci. USA* 78:3036–3039 (1976). Incorporation of an anti-sickling agent will increase the solution-gel ratio.

At equilibrium, the fraction of hemoglobin that has polymerized ($X_p$) was obtained from the relation:

$$X_p = \frac{C_p(C_t - C_s)}{C_t(C_p - C_s)}$$

after 8 hours centrifugation,
wherein:
  $C_p$ is the concentration of polymerized hemoglobin found in the sediment,
  $C_t$ is the concentration of polymerized hemoglobin present in the supernatant, and
  $C_s$ is the concentration of soluble hemoglobin present in the supernatant.

Delay time was also determined as an additional indication representing anti-sickling activity.

Results:

|  | $X_p$ | Delay Time |
|---|---|---|
| Control Sample | 25% | 0 |
| Extract Treated Sample (1.5 mg/300µ HbS) | 0% | >8 hours |

EXAMPLE III

Effect on Membrane Protein/Membrane Integrity: For the determination of the effect of the extract on the extractibility of spectrin from "ghosts" of sickle erythrocytes treated with the extract. The method used was described by Lux et al, *J. Clin. Invest.* 58:955–963 (1976). The effect of an anti-sickling agent will be observed as increased total level of the soluble spectrin and actin.

Results:

|  | % Total Extraction of Spectrin and Actin |
| --- | --- |
| Control Sample | 0 |
| Extract Treated Sample (27 mg/10⁶ cells) | 75 |

EXAMPLE IV

Effect on the Concentration of Free Internal Ca++:
It has been demonstrated that there is an approximate 3 to 4 fold increase of calcium and a corresponding loss of magnesium in sickled erythrocytes. Plasma content as well as erythrocyte calcium content were determined according to the method described by Corning Medical Laboratories using Corning Medical Calcium Ion Analyzer (Model 42). The effect of an anti-sickling agent will be observed as a decrease in the intracellular calcium ion concentration relative to sickled controls.

The extract treated samples maintained in human HbS cells the concentration of intracellular Ca++ to within the limits exhibited by normal red blood cells. Intracellular Ca++ in untreated sickled cells was three to four times as much as found in normal or extract treated cells.

Results:

|  | Intracellular Ca++ (Range) Meg/liter | Plasma Ca++ (Range) Meg/liter |
| --- | --- | --- |
| Control HbA (normal hemoblobin) | 0.6–1.4 | 4.37–4.97 |
| Control Hbs | 3.5–4.5 | 4.50–5.02 |
| Extract treated HbA | 0.5–1.2 | 4.2–4.5 |
| Extract treated HbS | 0.9–1.2 | 4.1–4.3 |

The results of this tests confirmed the ability of compositions prepared according to the process disclosed herein and in Allen, U.S. Pat. No. 3,102,691, to provide an effective anti-sickling composition useful in assessing the potential usefulness of in vivo administration of the anti-sickling agent for retarding red blood sickling in susceptible persons. Based on these experiments, medical researchers are provided an incentive to investigate a composition comprising a porphyrinic mixture of compounds in providing a significant advance in the treatment and prevention of sickle cell crisis.

Effective anti-sickling activity of the Allen product extract is demonstrated by the ability of the composition when interacting with HbS to both delay the onset of sickling and reduce the ultimate sickling effects after subjecting red blood cells to stress deoxygenation. Considering the physiological sequence of oxygenation and deoxygenation of red blood cells as they circulate through the body, a delay time of sickling in the order of minutes offers a significant advance in preventing the debilitating onset of sickle cell crisis. For example, in the normal course of sickle cell crisis, sickling will occur within seconds of deoxygenation stress. However, with administration of the Allen product extract, it is postulated that the time for sickling is delayed for a period of minutes, thereby allowing the red blood cells ample time to complete their circulation return to the lungs for oxygenation. Once the hemoglobin is reoxygenated the sickling process is averted.

The utility of this invention is underscored by the knowledge of the pharmacological activity of any compound or composition is beneficial to the public. It is inherently faster and easier to combat diseases and alleviate symptoms when the medical profession is armed with an arsenal of chemicals having known pharmacological activity. The recognition that the compositions disclosed by this application evidence pharmacological activity in retarding or averting sickling of red blood cells manifests a practical utility in aiding medical researchers to assess whether a patient may be amenable to potential in vivo therapeutic use by the anti-sickling composition.

The foregoing description of the invention has been directed to particular examples of demonstrating the anti-sickling ability of compositions comprising porphyrinic and chlorophyllic compounds for purposes of explanation and illustration. It is to be understood, however, that many changes and modifications in both the process and starting plant material can be made in implementing the present invention without departing from its concept of using porphyrinic and chlorophyllic extracts derived according to the processes described an anti-sickling agents. Accordingly, it is Applicant's intention that the following claims be interpreted to embrace all such modifications and variations:

What is claimed is:

1. An in vitro method of assessing the therapeutic potential of a composition of matter effective for retarding red blood cell sickling comprising:

providing an in vitro sample of red blood cells susceptible to sickling;

stressing the sample by deoxygenation to induce red blood cell sickling;

contacting the red blood cells with an anti-sickling effective amount of a composition of matter derived from alfalfa species *Medicago sativa* comprising a mixture of alkali metal salts of porphyrinic and chlorophyllic compounds dispersed in a physiologically compatible medium, said mixture characterized by:

containing from 35 to 65 percent porphyrinic compounds and the balance substantially chlorophyllic compounds;

having the form of a free-flowing solid;

being soluble in polar solvents and insoluble in nonpolar solvents;

having a dark blue-green color;

having a pH of 8.5 as a 1 percent by weight solution in water at 20° C.;

and when suspended in methanol exhibits a prominent absorption band at approximately 400 millimicrons and lesser adsorption bands at 660, 600 and 500 millimicrons; and observing a reduction of red blood cell sickling activity in the sample contacted with the anti-sickling agent compared to a control red blood cell sample not contacted with the anti-sickling composition.

2. The method according to claim 1 wherein the mixture comprises potassium salts of the porphyrinic and chlorophyllic compounds.

* * * * *